United States Patent [19]

Matsunaga et al.

[11] Patent Number: 5,028,623

[45] Date of Patent: Jul. 2, 1991

[54] INSECTICIDAL TRANSPARENT EMULSION

[75] Inventors: Tadahiro Matsunaga, Kobe; Kazunobu Dohara, Toyonaka, both of Japan

[73] Assignee: Sumitomo Chemical Company, Limited, Osaka, Japan

[21] Appl. No.: 384,143

[22] Filed: Jul. 24, 1989

[30] Foreign Application Priority Data

Aug. 5, 1988 [JP] Japan .................................. 63-196622

[51] Int. Cl.$^5$ ...................... A01N 37/34; A01N 53/00
[52] U.S. Cl. .................................... 514/521; 514/531; 514/937; 514/941
[58] Field of Search ................. 514/531, 937, 941, 521

[56] References Cited

U.S. PATENT DOCUMENTS

| | | | |
|---|---|---|---|
| 3,683,078 | 8/1972 | Haus | 514/71 |
| 4,299,839 | 11/1981 | Omura et al. | 514/531 |
| 4,500,348 | 2/1985 | Hausmann et al. | 71/103 |
| 4,737,520 | 4/1988 | Naik et al. | 514/520 |
| 4,870,103 | 9/1989 | Roechling et al. | 514/521 |
| 4,904,695 | 2/1990 | Bell | 514/521 |

FOREIGN PATENT DOCUMENTS

| | | |
|---|---|---|
| 1862/89 | 1/1989 | Austria . |
| 1007985 | 4/1977 | Canada . |
| 0062181 | 10/1982 | European Pat. Off. . |
| 0111580 | 6/1984 | European Pat. Off. . |
| 0149051 | 7/1985 | European Pat. Off. . |
| 0160182 | 11/1985 | European Pat. Off. . |
| 0215303 | 3/1987 | European Pat. Off. . |
| 3624910 | 1/1988 | Fed. Rep. of Germany . |
| 49-54547 | 5/1974 | Japan . |
| 197203 | 12/1982 | Japan . |
| 58-29761 | 6/1983 | Japan . |
| 60-54928 | 12/1985 | Japan . |
| 1355750 | 6/1974 | United Kingdom . |
| 2176706 | 1/1987 | United Kingdom . |

OTHER PUBLICATIONS

Chemical Abstracts (vol. 98): 139005x.
Chemical Abstract 87 (21); 1977, p. 141, Abstract No. 167 728 s.

*Primary Examiner*—Frederick E. Waddell
*Assistant Examiner*—Kevin Weddington
*Attorney, Agent, or Firm*—Stevens, Davis, Miller & Mosher

[57] ABSTRACT

The insecticidal transparent emulsion of the present invention is obtained by mixing (A) at least one pyrethroidal insecticide as defined in the claims as an active ingredient; (B) a polar solvent containing mixed surface active agent containing at least one metal alkylbenzenesulfonate, at least one nonionic surface active agent having an HLB (hydro- and lipophilicity balance) of 10 to 18 and at least one polar solvent; and (C) water, so that the content of (B) in the mixture is equal to or more than that of (A) and 6% by weight or less and then diluting the resulting mixture. The insecticidal transparent emulsion of the present invention has the advantage that the solution state is unchanged even when the environmental temperature sharply moves up and down.

4 Claims, No Drawings

INSECTICIDAL TRANSPARENT EMULSION

The present invention relates to an insecticidal transparent emulsion prepared by solubilizing a water-insoluble pyrethroidal insecticidal component in water with the aid of a particular mixed surface active agent, said insecticidal transparent emulsion being transparent and homogeneous as well as superior in the solution state and the stability of the active ingredient over a wide temperature range.

Pyrethroidal insecticides, because of their low toxicity to mammals, have been widely used in household spray insecticides.

Since the pyrethroidal insecticides are insoluble in water, they usually are dissolved in an organic solvent such as kerosene or aromatic solvents at first and (1) the resulting solution is directly sprayed with a sprayer, (2) the resulting solution is formed into an aerosol and sprayed with a jet gas, etc., or (3) the resulting solution is formed into an emulsion with an emulsifier, diluted with water and sprayed.

JP-B-58-29761 and JP-B-60-54928 disclosed a domestical application that a water-based solubilized-type insecticide is sprayed for killing insects.

When insecticides are sprayed indoors, however, insecticidal preparations which contain a large quantity of organic solvents and are used as in the above item (1) are not only unpleasant to sprayers but also undesirable in terms of safety and environmental hygiene. Aerosols which contain an inflammable gas in addition to organic solvents and are used as in the above item (2) are disadvantageous because they are inflammable at the time of use and are difficult to waste after the use. Further, the life of the emulsion as used in the item (3) after diluted with water is only about several hours at longest, so that the emulsion suffers from creaming and separation of oily layer, and cannot maintain the homogeneity over a long period of time. Because of this, the emulsion is usually used immediately after diluted with water. Further, there would be accompanied offensive odors of non-polar solvents such as aromatic solvents, kerosenes, etc. used, adverse effects on the sprayed surface that these solvents exert and change of the sprayed surface into white by the emulsifier.

The conventionally known water-based solubilized-type insecticides, which has been domestically and horticulturally used to control insect pests, come to lose the stable solution state by the environmental temperature change during the storage and produce precipitates. Thus their performances as insecticides are not reliable when the environmental temperature sharply moves up and down. These insecticides, therefore, have a problem in durability of sufficient quality to put them to practical use, and so may not always be said to be satisfactory.

According to the present invention, there is provided an insecticidal transparent emulsion comprising (A) at least one pyrethroidal insecticide selected from the group consisting of
3-phenoxybenzyl chrysanthemate,
3-allyl-2-methyl-4-oxocyclopent-2-enyl chrysanthemate,
3-allyl-2-methyl-4-oxocyclopent-2-enyl 2,2,3,3-tetramethylcyclopropanecarboxylate,
2-methyl-4-oxo-3-(2-propynyl)cyclopent-2-enyl chrysanthemate and
α-cyano-3-phenoxybenzyl chrysanthemate, or a mixture of at least one pyrethroidal insecticide selected from the group consisting of
3-phenoxybenzyl chrysanthemate,
3-allyl-2-methyl-4-oxocyclopent-2-enyl chrysanthemate,
3-allyl-2-methyl-4-oxocyclopent-2-enyl 2,2,3,3-tetramethylcyclopropanecarboxylate,
2-methyl-4-oxo-3-(2-propynyl)cyclopent-2-enyl chrysanthemate and
α-cyano-3-phenoxybenzyl chrysanthemate
and at least one pyrethroidal insecticide selected from the group consisting of
α-cyano-3-phenoxybenzyl 2,2,3,3-tetramethylcyclopropanecarboxylate,
3,4,5,6-tetrahydrophthalimidemethyl chrysanthemate,
3-phenoxybenzyl 3-(2,2-dichlorovinyl)-2,2-dimethylcyclopropanecarboxylate and
1-ethynyl-2-methyl-2-pentenyl chrysanthemate, as an active ingredient, (B) a polar solvent-containing mixed surface active agent containing at least one metal alkylbenzenesulfonate, at least one nonionic surface active agent having an HLB (hydro- and lipophilicity balance) of 10 to 18 and at least one polar solvent, and (C) water, the content of (B) in the emulsion being equal to or more than that of (A) and 6% by weight or less.

In the present invention, the mixed surface active agent containing a polar solvent refers to those containing at least one metal alkylbenzenesulfonate, at least one nonionic surface active agent having an HLB of 10 to 18 and at least one polar solvent. The metal alkylbenzenesulfonate is not critical. The number of carbon atoms of the alkyl group is not critical either, but it is preferably 8 to 13, more preferably 10 to 12. The metal of the metal salt is not critical, and it includes for example sodium and calcium.

The nonionic surface active agents used are those containing 6 to 40 moles of ethylene oxide, wherein the ethylene oxide is added so that the agent has an HLB of 10 to 18. The HLB is preferably 12 to 16. Specific examples of the agent are polyoxyethylene styrenated phenol, polyoxyethylene alkylphenyl ether, polyoxyethylene alkyl ether, etc. Specific examples of the polar solvent are propylene glycol, butyl glycol, butyl diglycol, isopropyl alcohol, ethanol, methoxybutanol, etc.

The mixing weight ratio between the metal alkylbenzenesulfonate, the nonionic surface active agent and the polar solvent is not critical, and it is preferably 25–40:40–55:5–30, more preferably 28–37:43–50:15–23. The mixing weight ratio of the metal alkylbenzenesulfonate to the nonionic surface active agent is preferably 1:2 to 1:1.

The insecticidal transparent emulsion of the present invention contains the foregoing polar solvent-containing mixed surface active agent in a weight equal to or more than that of the pyrethroidal insecticide which is an active ingredient, and besides in an amount of 6% by weight or less of the emulsion. Preferably, the emulsion contains the polar solvent-containing mixed surface active agent in a weight 3 to 6 times that of the pyrethroidal insecticide.

Specific examples of the pyrethroidal insecticide used in the present invention are 3-phenoxybenzyl chrysanthemate (phenothrin), 3-allyl-2-methyl-4-oxocyclopent-2-enyl chrysanthemate (allethrin), 3-allyl-2-methyl-4-oxocyclopent-2-enyl 2,2,3,3-tetramethylcyclopropanecarboxylate (terallethrin), 2-methyl- 4-oxo-3-(2-propynyl)cyclopent-2-enyl chrysanthemate (prallethrin), α-cyano-3-phenoxybenzyl chrysanthemate (cyphenothrin) α-cyano-3-phenoxybenzyl 2,2,3,3-tetramethylcyclopropanecarboxylate (fenpropathrin), 3,4,5,6-tetrahydrophthalimidemethyl chrysanthemate (tetramethrin), 3-phenoxybenzyl 3-(2,2-dichlorovinyl)-2,2-dimethyl-cyclopropanecarboxylate (permethrin), 1-ethynyl-2-methyl-2-pentenyl chrysanthemate (empenthrin) and their isomers such as geometrical isomers and optical isomers.

The insecticidal transparent emulsion of the present invention may contain, if necessary, a synergist such as piperonyl butoxide (hereinafter referred to as PBO), octachlorodipropyl ether, etc., whereby the activity is expected to be strengthened.

Further, the stability of the active ingredient can be maintained by optionally adding an antioxidant [e.g. 2,6-di-tert-butyl-4-methylphenol (BHT), 2,2'-methylenebis(4-methyl-6-tert-butylphenol), n-octadecyl 3-(3',5'-di-tert-butyl-4'-hydroxyphenyl)propionate], salts (e.g. sodium benzoate, ammonium benzoate), etc. Further, the insecticidal transparent emulsion of the present invention can prevent water-mold by adding disinfectant such as Proxel® GXL (manufactured by ICI Americans Inc.). Moreover it can also be used for horticultural purposes together with fungicides.

For producing the insecticidal transparent emulsion of the present invention, it is most general to prepare a concentrate by mixing the pyrethroidal insecticide which is an active ingredient, the polar solvent-containing mixed surface active agent and if necessary, oil-soluble additives (e.g. BHT), and dilute the resulting concentrate with water (Process A).

In an alternative process (Process B), a concentrate is prepared by mixing the pyrethroidal insecticide as an active ingredient, the polar solvent-containing mixed surface active agent, oil-soluble additives (e.g. BHT) which is added as need arises and a substance for increasing the weight of the concentrate, for example a polar solvent, water or a mixture of the both, and then the resulting concentrate is diluted with water.

In Process A, the concentrate has a high viscosity, and when it is weighed, calculation of the amount to be weighed is troublesome. According to Process B, by contrast, the weighing operation can be improved.

For example, when the insecticidal transparent emulsion containing 0.2% of allethrin and 0.2% of phenothrin is produced, a concentrate is first produced by mixing 5 parts by weight of each of allethrin and phenothrin, 40 parts by weight of the polar solvent-containing mixed surface active agent, 1 part by weight of BHT and any of propylene glycol, a propylene glycol/water (1:1 by weight) mixture and water in a quantity sufficient for making the total weight 100 parts, and then 4 parts by weight of the concentrate is mixed with 96 parts by weight of water to prepare the desired insecticidal transparent emulsion.

When the insecticidal transparent emulsion of the present invention thus prepared is domestically used, it is effective to fill the emulsion in a small hand sprayer and directly spray onto the body of flying insects (e.g. flies, mosquitoes) and crawling insects (e.g. cockroaches), or apply to the refuge of the crawling insects. The insecticidal transparent emulsion of the present invention is also useful to exterminate bedbugs, fleas, lice, etc.

The concentrate of the insecticidal transparent emulsion obtained by the foregoing Process B can be used without diluted with water for ULV spraying (ultra low volume spraying).

The insecticidal transparent emulsion of the present invention contains the pyrethroidal insecticides, active ingredients, in an amount of preferably 0.02 to 2% by weight, more preferably 0.05 to 1% by weight.

The present invention will be illustrated in more detail with reference to the following examples, but it is not limited to these examples.

EXAMPLE 1

Insecticidal transparent emulsions having a composition shown in Table 1 were prepared using Hymal 1119, 1141, 1156 or 1159 (a product of Matsumoto Yushi Seiyaku Co., Ltd.; a mixture of calcium dodecylbenzenesulfonate, polyoxyethylene styrenated phenol having an HLB of 12 to 16 and propylene glycol) as the polar solvent-containing mixed surface active agent.

TABLE 1

| Formulation example No. | Polar solvent-containing mixed surface active agent* (% w/w) | Active ingredient | (% w/w) | Additives | (% w/w) |
|---|---|---|---|---|---|
| 1 | 0.8 | Tetramethrin | 0.1 | | |
| | | d-Phenothrin | 0.1 | | |
| 2 | 0.8 | d-Allethrin | 0.1 | | |
| | | Permethrin | 0.1 | | |
| 3 | 0.8 | Terallethrin | 0.2 | | |
| 4 | 0.8 | d-Allethrin | 0.1 | | |
| | | d-Phenothrin | 0.1 | | |
| 5 | 1.5 | d-Allethrin | 0.25 | | |
| | | d-Phenothrin | 0.25 | | |
| 6 | 2.0 | d-Allethrin | 0.25 | | |
| | | d-Phenothrin | 0.25 | | |
| 7 | 3.0 | d-Allethrin | 0.25 | | |
| | | d-Phenothrin | 0.25 | | |
| 8 | 3.0 | d-Allethrin | 0.5 | | |
| | | d-Phenothrin | 0.5 | | |
| 9 | 0.8 | d-Phenothrin | 0.2 | BHT | 0.01 |
| 10 | 0.8 | d-Tetramethrin | 0.1 | BHT | 0.01 |
| | | d-Phenothrin | 0.1 | | |
| 11 | 0.8 | Prallethrin | 0.05 | BHT | 0.01 |
| | | PBO | 0.15 | | |
| 12 | 0.8 | d-Allethrin | 0.1 | BHT | 0.01 |
| | | Phenpropathrin | 0.1 | | |
| 13 | 0.8 | d-Allethrin | 0.1 | BHT | 0.01 |

TABLE 1-continued

| Formulation example No. | Polar solvent-containing mixed surface active agent* (% w/w) | Active ingredient (% w/w) | | Additives (% w/w) | |
|---|---|---|---|---|---|
| | | d-Phenothrin | 0.1 | Propylene glycol | 0.01 |
| 14 | 0.8 | d-Allethrin | 0.1 | Isopropyl alcohol | 0.01 |
| | | d-Phenothrin | 0.1 | | |
| 15 | 0.8 | d-Allethrin | 0.2 | Ammonium benzoate | 0.7 |
| 16 | 0.8 | d-Allethrin | 0.1 | Ammonium benzoate | 0.7 |
| | | d-Cyphenothrin | 0.1 | | |
| 17 | 0.8 | d-Allethrin | 0.1 | BHT | 0.02 |
| | | d-Phenothrin | 0.1 | Propylene glycol | 0.98 |
| | | | | Proxel GXL | 0.1 |
| 18 | 0.8 | d-Cyphenothrin | 0.2 | | |
| 19 | 0.8 | d-Cyphenothrin | 0.2 | BHT | 0.02 |
| 20 | 0.35 | Prallethrin | 0.05 | | |
| 21 | 0.70 | Prallethrin | 0.1 | | |
| 22 | 0.70 | Prallethrin | 0.1 | BHT | 0.01 |
| 23 | 0.70 | Prallethrin | 0.1 | Proxel GXL | 0.2 |
| 24 | 0.70 | Prallethrin | 0.05 | BHT | 0.01 |
| | | | | Proxel GXL | 0.2 |
| 25 | 1.40 | Prallethrin | 0.2 | | |
| 26 | 1.80 | Prallethrin | 0.1 | | |
| | | PBO | 0.3 | | |

Used polar solvent containing mixed surface active agent
No. 1-17 Hymal 1119
No. 18, 19 Hymal 1141
No. 20-25 Hymal 1156
No. 26 Hymal 1159

In Formulation examples 1 to 8, firstly a single and mixed active ingredients were each mixed with Hymal 1119 in a ratio shown in Table 1 while heating to about 40° C. with stirring. After the solution phase had become uniform, the concentrates were diluted with water to the respective active ingredient concentrations shown in Table 1 to obtain uniform and transparent insecticidal transparent emulsions.

In Formulation examples 9 to 12, a single active ingredient, alone or mixed with PBO, and mixed active ingredients were each mixed with Hymal 1119 and BHT in a ratio shown in Table 1 while heating to about 40° C. with stirring. After the solution phase had become uniform, the concentrates were diluted with water to the respective active ingredient concentrations shown in Table 1 to obtain uniform and transparent insecticidal transparent emulsions.

In Formulation example 13, d-allethrin and d-phenothrin which are an active ingredient, Hymal 1119, BHT and propylene glycol were mixed in a ratio shown in Table 1 while heating to about 40° C. with stirring. After the solution phase had become uniform, the concentrate was diluted with water to the active ingredient concentration shown in Table 1 to obtain a uniform and transparent insecticidal transparent emulsion.

In Formulation example 14, a uniform and transparent insecticidal transparent emulsion was obtained in the same manner as in Formulation example 13 except that isopropyl alcohol was used in place of propylene glycol, and BHT was not added.

In Formulation examples 15 and 16, a single active ingredient and a mixture of two active ingredients were each mixed with Hymal 1119 in a ratio shown in Table 1 while heating to about 40° C. with stirring. Thus, concentrates having a uniform solution phase were obtained. The concentrates were then diluted with a 0.7% aqueous ammonium benzoate solution to the active ingredient concentrations shown in Table 1 to obtain uniform and transparent insecticidal transparent emulsions.

In Formulation example 17, a mixture of dallethrin and d-phenothrin which is an active ingredient, Hymal 1119, BHT and Proxel GXL were mixed in a ratio shown in Table 1 while heating to about 40° C. with stirring. After the solution phase had become uniform, the concentrate was diluted with water to the active ingredient concentration shown in Table 1 to obtain a uniform and transparent insecticidal transparent emulsion.

In Formulation examples 18 and 19, a single active ingredient d-Cyphenothrin, Hymal 1141 and BHT were mixed in a ratio shown in Table 1 while heating to about 40° C. with stirring. After the solution phase had become uniform, the concentrate was diluted with water to the active ingredient concentration shown in Table 1 to obtain a uniform and transparent insecticidal transparent emulsion.

In Formulation examples 20 to 25, a single active ingredient Prallethrin, Hymal 1156, BHT and Proxel GXL were mixed in a ratio shown in Table 1 while heating to about 40° C. with stirring. After the solution phase had become uniform, the concentrate was diluted with water to the active ingredient concentration shown in Table 1 to obtain a uniform and transparent insecticidal transparent emulsion.

In Formulation example 26, a mixture of Prallethin and PBO which is an active ingredient and Hymal 1159 were mixed in a ratio shown in Table 1 while heating to about 40° C. with stirring. After the solution phase had become uniform, the concentrate was diluted with water to the active ingredient concentration shown in Table 1 to obtain a uniform and transparent insecticidal transparent emulsion.

Formulation examples in which surface active agents not included in the scope of the present invention were used, are shown in Table 2 as comparative examples.

In Comparative formulation examples A to E, a single or mixed active ingredients and surface active agents not included in the scope of the present invention were mixed in ratios shown in Table 2 while heating to about 40° C. with stirring. The resulting concentrates were diluted with water to the active ingredient concentrations shown in Table 2 to obtain comparative preparations.

TABLE 2

| Comparative formulation example | Surface active agent, etc. (% w/w) | | Active ingredient (% w/w) | |
|---|---|---|---|---|
| A | Polyoxyethylene polypropylene glycol monooleate (HLB, 18.5) | 0.2 | Tetramethrin | 0.1 |
|   |   |   | d-Resmethrin | 0.1 |
|   | Polyoxyethylene (10 moles).styrenated phenol | 0.4 |   |   |
| B | Polyoxyethylene (40 moles).castor oil | 1.0 | Phenothrin | 0.3 |
|   | Polyoxyethylene.styrenated phenol (HLB, 14.0) | 0.5 |   |   |
| C | Polyoxyethylene (10 moles).styrenated phenol | 0.4 | Tetramethrin | 0.1 |
|   |   |   | d-Phenothrin | 0.1 |
|   | Polyoxyethylene stearic acid ester (HLB, 15.6) | 0.2 |   |   |
| D | Polyoxyethylene polypropylene glycol monooleate (HLB, 18.5) | 0.5 | Tetramethrin | 0.1 |
|   |   |   | d-Resmethrin | 0.1 |
|   | Polyoxyethylene (20 moles).sorbitan monostearate | 0.5 | d-Allethrin | 0.1 |
| E | Polyoxyethylene polypropylene glycol monooleate (HLB, 18.5) | 0.2 | d-Allethrin | 0.2 |
|   | Polyoxyethylene (40 moles).castor oil | 0.2 |   |   |

EXAMPLE 2

The insecticidal transparent emulsions and comparative emulsions prepared in Example 1 were stored in the following different conditions and observed for the solution state: (1) Two weeks' storage at different temperatures, 10° C., 25° C. and 40° C. in a constant-temperature vessel or room, and (2) 2 weeks' storage at a temperature of −20° C. and then 24 hours' standing at 25° C. or shaking subsequent to the standing. Further, after the test emulsions had been stored under a severe condition of 60° C.×2 weeks, the percentages of the residual active ingredient were measured by gas chromatography as follows.

To 1 g of the sample was added 10 or 20 ml of a 0.1% (w/v) acetone solution of an internal standard substance, and the mixture was concentrated under reduced pressure. The residue was then dissolved in 2 ml of acetone. The resulting test solution was quantitatively analyzed by gas chromatography according to the internal standard substance method with an FID detector. The measurement conditions were as follows.

| Ingredient to be analyzed | Internal standard substance | Temperature of column (°C.) | Temperature of gasification room (°C.) |
|---|---|---|---|
| Tetramethrin | Triphenyl- | 180° C. | 230° C. |
| (or d-tetramethrin) and d-phenothrin | methane | | |
| Terallethrin | Same as above | Same as above | Same as above |
| d-Allethrin and d-phenothrin | triphenyl phosphate | 220° C. | 270° C. |
| d-Allethrin | Same as above | Same as above | Same as above |
| d-Allethrin and d-cyphenothrin | Same as above | Same as above | Same as above |
| d-Cyphenothrin | Same as above | Same as above | Same as above |
| Prallethrin and PBO | Diphenyl phthalate | 200° C. | 250° C. |
| Prallethrin | Same as above | Same as above | Same as above |
| d-Allethrin and permethrin | Triphenyl phosphate* | 200° C.* | 270° C.* |
|   | Diphenyl phthalate** | 215° C.** | 270° C.** |

Note:
*Conditions at the analysis of d-allethrin.
**Conditions at the analysis of permethrin.

The results are shown in Table 3. The solution state is shown by the following symbols.
○:Transparent
Δ:Translucent
x:Opaque (white turbid) or formation of precipitates.

TABLE 3

| Test example | Formulation examples shown in Tables 1 and 2 | Initial solution state | Solution state after 2 weeks | | | −20° C. → 25° C. | | 60° C. → 25° C. | | Percentage of residual active ingredient after 2 weeks at 60° C. (%) | |
|---|---|---|---|---|---|---|---|---|---|---|---|
|   |   |   | 10° C. | 25° C. | 40° C. | Standing | Shaking | Standing | Shaking |   |   |
| 1 | 1 | o | o | o | o | o | o | o | o | Tetramethrin | 92 |
|   |   |   |   |   |   |   |   |   |   | d-Cyphenothrin | 100 |
| 2 | 2 | o | o | o | o | o | o | o | o | d-Allethrin | 98 |
|   |   |   |   |   |   |   |   |   |   | Permethrin | 100 |
| 3 | 3 | o | o | o | o | o | o | o | o | Terallethrin | 103 |

TABLE 3-continued

| Test example | Formulation examples shown in Tables 1 and 2 | Initial solution state | Solution state after 2 weeks | | | −20° C. → 25° C. | | 60° C. → 25° C. | | Percentage of residual active ingredient after 2 weeks at 60° C. (%) | |
|---|---|---|---|---|---|---|---|---|---|---|---|
| | | | 10° C. | 25° C. | 40° C. | Standing | Shaking | Standing | Shaking | | |
| 4 | 7 | o | o | o | o | o | o | o | o | d-Allethrin | 97 |
| | | | | | | | | | | d-Phenothrin | 99 |
| 5 | 8 | o | o | o | o | o | o | o | o | d-Allethrin | 98 |
| | | | | | | | | | | d-Phenothrin | 100 |
| 6 | 10 | o | o | o | o | o | o | o | o | d-Tetramethrin | 96 |
| | | | | | | | | | | d-Phenotrhin | 98 |
| 7 | 11 | o | o | o | o | o | o | o | o | Prallethrin | 97 |
| | | | | | | | | | | PBO | 99 |
| 8 | 13 | o | o | o | o | o | o | o | o | d-Allethrin | 102 |
| | | | | | | | | | | d-Phenothrin | 101 |
| 9 | 15 | o | o | o | o | o | o | o | o | d-Allethrin | 97 |
| 10 | 16 | o | o | o | o | o | o | o | o | d-Allethrin | 97 |
| | | | | | | | | | | d-Cyphenothrin | 100 |
| 11 | 17 | o | o | o | o | o | o | o | o | d-Allethrin | 99 |
| | | | | | | | | | | d-Phenotrhin | 99 |
| 12 | 18 | o | o | o | o | o | o | o | o | d-Cyphenothrin | 100 |
| 13 | 19 | o | o | o | o | o | o | o | o | d-Cyphenothrin | 100 |
| 14 | 20 | o | o | o | o | o | o | o | o | Prallethrin | 98 |
| 15 | 21 | o | o | o | o | o | o | o | o | Prallethrin | 98 |
| 16 | 22 | o | o | o | o | o | o | o | o | Prallethrin | 99 |
| 17 | 23 | o | o | o | o | o | o | o | o | Prallethrin | 100 |
| 18 | 24 | o | o | o | o | o | o | o | o | Prallethrin | 97 |
| 19 | 25 | o | o | o | o | o | o | o | o | Prallethrin | 98 |
| 20 | 26 | o | o | o | o | o | o | o | o | Prallethrin | 100 |
| | | | | | | | | | | PBO | 98 |
| 21 | A | Δ | Δ | x | x | x | Δ | x | x | | |
| 22 | B | o | x | Δ | Δ | Δ | Δ | Δ | Δ | | |
| 23 | C | Δ | x | x | x | Δ | Δ | x | x | | |
| 24 | D | o | x | Δ | Δ | x | x | Δ | Δ | | |
| 25 | E | o | x | Δ | Δ | x | x | Δ | Δ | | |

EXAMPLE 3

Twenty adults per group (sex ratio=1:1) of housefly (*Musca domestica*) were liberated in a 0.34 m³ glass test chamber, and a prescribed amount of the insecticidal transparent emulsion prepared according to Formulation example was sprayed onto the adults by means of a trigger sprayer (Canyon CHS-3B; produced by Canyon Co., Ltd.). After spraying, the number of knocked-down insects was counted with the lapse of time, and after 20 minutes, the whole test insects were recovered in a clean cup. After giving water and baits, the cup was transferred to an observation room, and a mortality after 24 hours was examined. The $KT_{50}$ value was calculated according to the Bliss' probit method. This test was repeated three time to five times.

The results are shown in Table 4.

change which is an important quality, so that it may be said to have solved the long-standing problem.

What is claimed is:

1. An insecticidal transparent emulsion comprising
(A) at least one pyrethroidal insecticide selected from the group consisting of
    3-phenoxybenzyl chrysanthemate,
    3-allyl-2-methyl-4-oxocyclopent-2-enyl chrysanthemate,
    3-allyl-2-methyl-4-oxocyclopent-2-enyl 2,2,3,3-tetramethylcyclopropanecarboxylate,
    2-methyl-4-oxo-3-(2-propynyl)cyclopent-2-enyl chrysanthemate and
    α-cyano-3-phenoxybenzyl chrysanthemate, or
a mixture of at least one pyrethroidal insecticide selected from the group consisting of
    3-phenoxybenzyl, chrysanthemate,

TABLE 4

| Test agent | | | | | | | | | | | |
|---|---|---|---|---|---|---|---|---|---|---|---|
| Active ingredient (% w/w) | Polar solvent-containing mixed surface active agent (% w/w) | Amount sprayed | Knock-down ratio (%, min) | | | | | | | $KT_{50}$ (min) | Mortality (after 24 hours) (%) |
| | | | 0.7 | 1 | 1.5 | 2 | 3 | 5 | 7 | 10 | |
| d-Tetramethrin | 0.2 | 0.7 g | 1 | 12 | 30 | 43 | 66 | 84 | 95 | 97 | 2.3 | 100 |
| d-Phenothrin | 0.2 | | | | | | | | | | | |
| d-Tetramethrin | 0.2 | 1.4 g | 9 | 26 | 50 | 65 | 83 | 95 | 98 | 100 | 1.6 | 100 |
| d-Phenothrin | 0.2 | | | | | | | | | | | |
| Oil agent (control)* | — | 0.7 ml | 7 | 22 | 40 | 45 | 48 | 65 | 81 | 88 | 2.7 | 63 |
| Pyrethrin | — | 1.4 ml | 17 | 25 | 37 | 43 | 65 | 80 | 93 | 97 | 2.0 | 40 |

*The oil agent as a control was prepared by dissolving natural pyrethrin in a solvent comprising Nisseki fog solvent (kerosene for insecticides; produced by Nippon Sekiyu Kagaku Co., Ltd.) so that the content of the pyrethrin was 0.1% w/w, as converted to a pure active ingredient.

The insecticidal transparent emulsion of the present invention is stable in a solution state to temperature 3-allyl-2-methyl-4-oxocyclopent-2-enyl chrysanthemate,
3-allyl-2-methyl-4-oxocyclopent-2-enyl 2,2,3,3-tetramethylcyclopropanecarboxylate,
2-methyl-4-oxo-3-(2-propynyl)cyclopent-2-enyl chrysanthemate and
α-cyano-3-phenoxybenzyl chrysanthemate
and at least one pyrethroidal insecticide selected from the group of consisting of
α-cyano-3-phenoxybenzyl 2,2,3,3-tetramethylcylopropanecarboxylate,
3,4,5,6-tetrahydrophthalimidemethyl chrysanthemate,
3-phenoxybenzyl 3-(2,2-dichlorovinyl)-2,2-dimethylcyclopropanecarboxylate and
1-ethynyl-2-methyl-2-pentenyl chrysanthemate, as an active ingredient,
(B) a polar solvent-containing mixed surface active agent containing calcium dodecylbenzenesulfonate, polyoxyethylene styrenated phenol having an HLB (hydro- and lipophilicity balance) of 12 to 16 and propylene glycol, and
(C) water,
the content of (B) in the emulsion being equal to or more than that of (A) and 6% by weight or less.

2. An insecticidal transparent emulsion according to claim 1, wherein the active ingredient is at least one pyrethroidal insecticide selected from the group consisting of
3-phenoxybenzyl chrysanthemate,
3-allyl-2-methyl-4-oxocyclopent-2-enyl chrysanthemate,
3-allyl-2-methyl-4-oxocyclopent-2-enyl 2,2,3,3-tetramethylcyclopropanecarboxylate,
2-methyl-4-oxo-3-(2-propynyl)cyclopent-2-enyl chrysanthemate and
α-cyano-3-phenoxybenzyl chrysanthemate.

3. An insecticidal transparent emulsion according to claim 1, wherein the weight ratio between calcium dodecylbenzenesulfonate, polyoxyethylene styrenated phenol having an HLB (hydro- and lipophilicity balance) of 12 to 16 and propylene glycol is 25–40:40–55:5–30.

4. An insecticidal transparent emulsion according to claim 1, wherein the active ingredient is at least one pyrethroidal insecticide selected from the group consisting of
3-phenoxybenyl chrysanthemate,
3-allyl-2-methyl-4-oxocyclopent-enyl-chrysanthemate,
3-allyl-2-methyl-4-oxocyclopent-2-enyl 2,2,3,3-tetramethylcyclopropanecarboxylate,
2-methyl-4-oxo-3-(2-propynyl)cyclopent-2-enyl chrysanthemate and
α-cyano-3-phenoxybenzyl chrysanthemate,
wherein the weight ratio between calcium dodecylbenzenesulfonate, polyoxyethylene styrenated phenol having an HLB of 12 to 16 and propylene glycol is 25–40:40–55:5–30.

* * * * *